(12) United States Patent
Bacher et al.

(10) Patent No.: US 8,449,530 B2
(45) Date of Patent: May 28, 2013

(54) MEDICAL INSTRUMENT WITH A LOCKABLE BEND CONTROL MECHANISM

(75) Inventors: Uwe Bacher, Tuttlingen (DE); Egon Deufel, Fridingen (DE); Sabine Zahler, Vaterstetten (DE)

(73) Assignee: Karl Storz GmbH & Co. KG (DE)

( * ) Notice: Subject to any disclaimer, the term of this patent is extended or adjusted under 35 U.S.C. 154(b) by 1030 days.

(21) Appl. No.: 12/415,110

(22) Filed: Mar. 31, 2009

(65) Prior Publication Data
US 2009/0247994 A1 Oct. 1, 2009

(30) Foreign Application Priority Data
Mar. 31, 2008 (DE) .......................... 10 2008 017 300

(51) Int. Cl.
*A61B 17/00* (2006.01)
(52) U.S. Cl.
USPC .............................................. 606/1; 606/205
(58) Field of Classification Search
USPC ...... 600/131, 139–152; 606/51–53, 113–114, 606/139–148, 205–213; 604/61, 95.01–95.05, 604/523, 528; 227/175.1, 176.1, 178.1, 179.1, 227/180.1
See application file for complete search history.

(56) References Cited

U.S. PATENT DOCUMENTS

| 3,557,780 | A | | 1/1971 | Sato |
| 4,942,866 | A | | 7/1990 | Usami |
| 5,314,445 | A | * | 5/1994 | Heidmueller nee Degwitz et al. ............................ 606/208 |
| 5,329,887 | A | * | 7/1994 | Ailinger et al. ............... 600/148 |
| 5,347,989 | A | * | 9/1994 | Monroe et al. ................. 600/131 |
| 5,383,852 | A | * | 1/1995 | Stevens-Wright .......... 604/95.04 |
| 5,618,294 | A | | 4/1997 | Aust et al. |
| 5,743,456 | A | | 4/1998 | Jones et al. |
| 5,766,196 | A | | 6/1998 | Griffiths |
| 5,888,192 | A | | 3/1999 | Heimberger |
| 6,077,287 | A | | 6/2000 | Taylor et al. |
| 8,137,263 | B2 | * | 3/2012 | Marescaux et al. ............ 600/101 |
| 2002/0165484 | A1 | * | 11/2002 | Bowe et al. ................. 604/95.05 |
| 2003/0135199 | A1 | * | 7/2003 | Rosenman et al. ............ 604/528 |
| 2004/0193016 | A1 | * | 9/2004 | Root et al. ..................... 600/146 |
| 2005/0288627 | A1 | * | 12/2005 | Mogul ......................... 604/95.04 |
| 2006/0287643 | A1 | * | 12/2006 | Perlin ................................. 606/1 |
| 2007/0246508 | A1 | * | 10/2007 | Green .......................... 227/180.1 |

FOREIGN PATENT DOCUMENTS

| DE | 3905455 A1 | 8/1989 |
| DE | 19650721 A1 | 6/1998 |
| EP | 0306723 A1 | 3/1989 |
| EP | 1854415 A1 | 11/2007 |
| EP | 2027820 A1 | 2/2009 |
| WO | 2008020964 A2 | 2/2008 |

OTHER PUBLICATIONS http://www.thefreedictionary.com/screw, retrieved Jul. 27, 2012.*
European Search Report; EP 09 15 6415; Jul. 23, 2009; 8 pages.

* cited by examiner

*Primary Examiner* — Ryan Severson
*Assistant Examiner* — David Eastwood
(74) *Attorney, Agent, or Firm* — St. Onge Steward Johnston & Reens LLC

(57) ABSTRACT

A medical instrument comprises a shaft whose distal end is bendable. Arranged at the proximal end of the shaft there is a handle on which a bend control mechanism for controlling the bending movement is arranged. The bend control mechanism has a pivotable control element. The pivotable control element runs over a friction element, and an actuating element is provided via which the friction element can be brought out of a locking engagement with the control element.

21 Claims, 11 Drawing Sheets

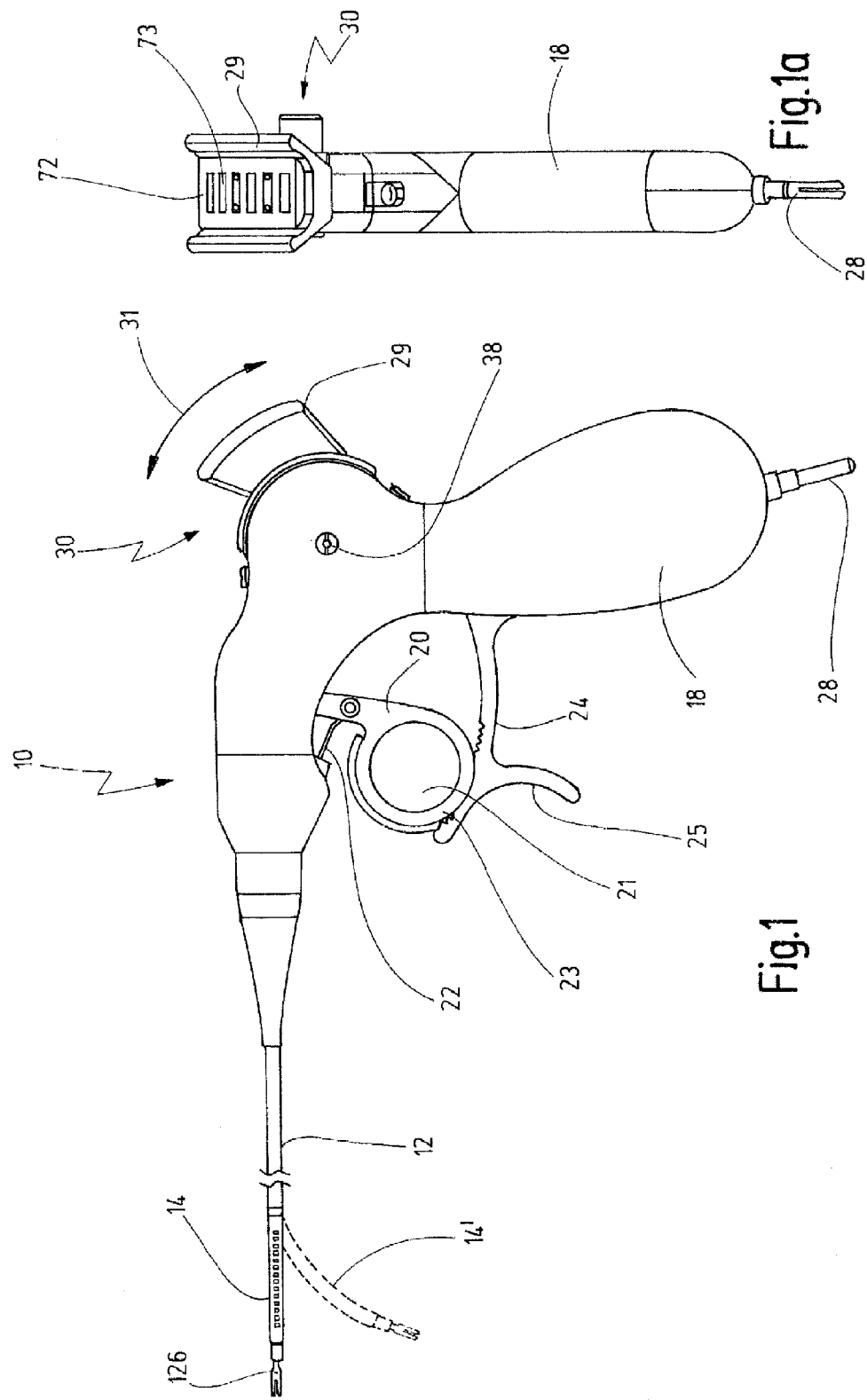

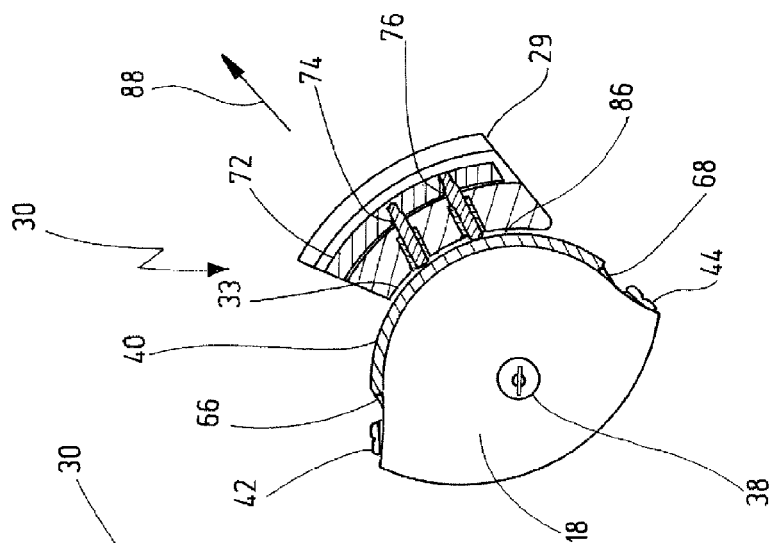
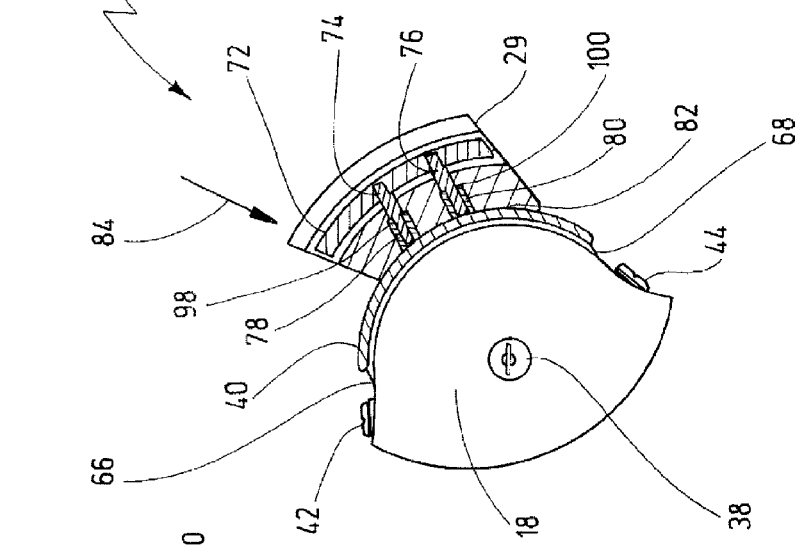
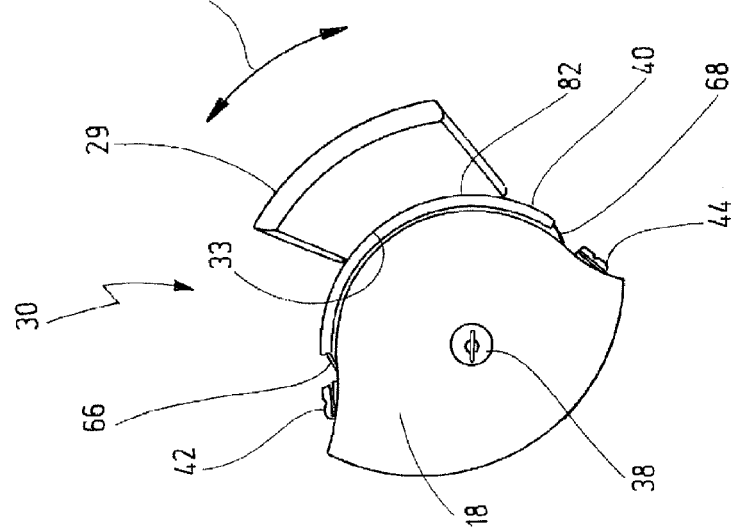

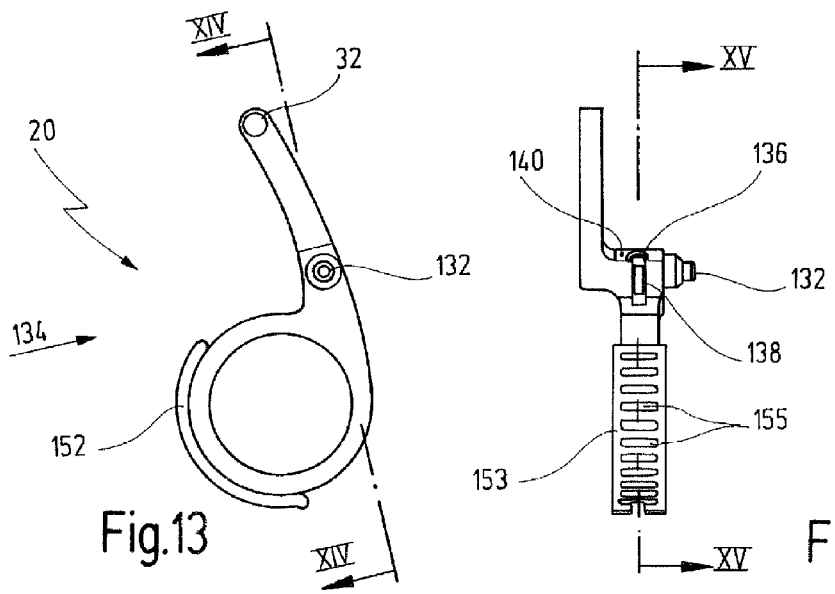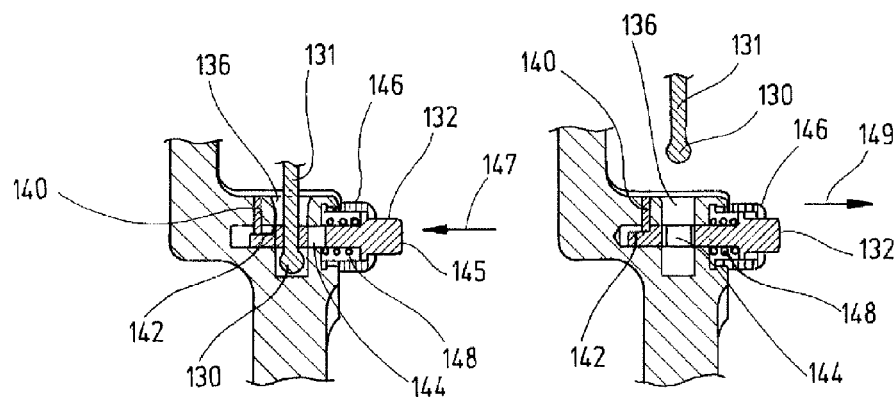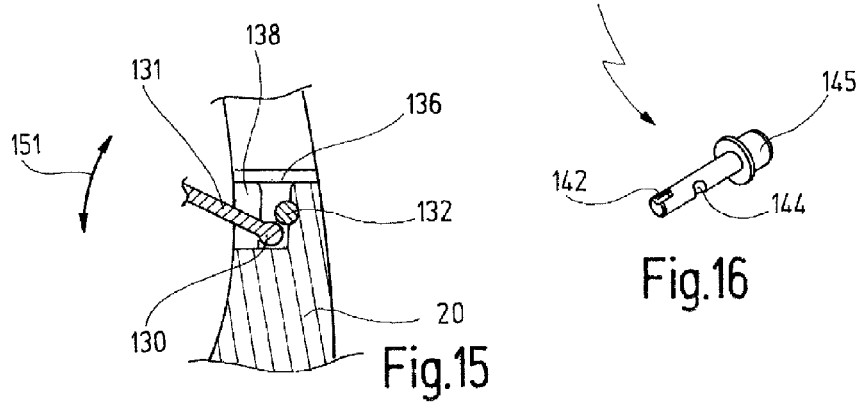

MEDICAL INSTRUMENT WITH A LOCKABLE BEND CONTROL MECHANISM

BACKGROUND OF THE INVENTION

The invention relates to a medical instrument with a shaft whose distal end is bendable, with a handle which is arranged at the proximal end of the shaft and on which a bend control mechanism for controlling the bending movement of the bendable end is arranged, the bend control mechanism having a pivotable control element whose pivoting causes the bending movement, and with a locking mechanism for locking the bend control mechanism in defined positions.

A medical instrument of this kind is known from U.S. Pat. No. 5,766,196.

Medical instruments with a bendable end of the shaft provide the operator with considerably more degrees of freedom of handling in the area of the distal end of the instrument.

In instruments with a rigid shaft, which are mainly used for minimally invasive interventions, this affords the possibility of using the instrument to perform manipulations, within a cavity, that lie outside the longitudinal axis of the shaft.

In the case of flexible shafts, it is possible for these to be introduced into the body through body channels, for example the bronchi, the esophagus or the intestine, and, by additional bending of the distal end of the shaft, the abovementioned additional degrees of freedom of handling are permitted.

The manipulations are of many types. For example, it is possible to perform gripping or dissecting procedures, visual inspections on their own or combined with the aforementioned procedures, coagulation procedures and the like.

To control the bending movement of the shaft, a bend control mechanism is provided that comprises control wires which, in the bendable area of the shaft, are fastened at sites on either side of the central longitudinal axis of the shaft. By pulling one control wire and pushing another control wire, the curving or bending of the shaft can be triggered. At the proximal end, the control wires are mounted on a disc-shaped or drum-shaped body and are fixed there. Turning this body results in one control wire being pulled and the other control wire being pushed.

To turn the drum, the latter is connected to a pivotable control element which can be pivoted to and fro using, for example, a finger of the hand that is holding the medical instrument.

When performing the manipulations, it is desirable for the bendable shaft to remain in defined bent positions, for which purpose a locking mechanism is provided.

In the instrument mentioned in U.S. Pat. No. 5,766,196, this is achieved by the fact that the drum has radially outwardly pretensioned locking pins which engage in hollows or recesses, in the extreme end positions of the bending movement, in order to hold the bent shaft in these positions. In one embodiment, several such locking positions are arranged circumferentially, such that the bent area of the shaft can be locked in numerous bent positions. It is further mentioned in this document that the control wires can be held in a desired position in the bendable area by being held by a resistance force, possibly with a braking mechanism.

It is the object of the present invention is to develop a medical instrument of the type mentioned at the outset in such a way that the bendable portion of the shaft can be locked in any desired position, this being permitted by a safe and ergonomically actuated control mechanism.

SUMMARY OF THE INVENTION

This object is achieved by a medical instrument comprising a shaft having a distal end being bendable, a handle arranged at the proximal end of said shaft, a bend control mechanism for controlling a bending movement of said bendable distal end of said shaft, said bend control mechanism being arranged at said handle and having a pivotable control element, a pivoting of said pivotable control element causes a bending of said bendable distal end of said shaft, and a locking mechanism for locking said bend control mechanism in defined positions, wherein said pivotable control element runs over a friction element, and wherein an actuating element being provided via which said friction element can be brought out of a locking engagement with said pivotable control element.

The fact that the pivotable control element runs over a friction element means that it can be locked in any of its pivot positions, provided it is in frictional engagement with the friction element. The friction element thus functions in the manner of a brake, which leads to the locking frictional engagement in any desired state of pivoting of the control element. By providing an additional actuating element, the friction element can be moved out of a locking engagement with the control element, and the control element can then be pivoted again in order to bring about or control a change in the degree of bending of the bendable end via the bend control mechanism.

This locking action is also particularly ergonomic, since the pivotable control element and the friction element are in frictional engagement without actuation of the actuating element. Therefore, when the medical instrument is being handled and the actuating element is not actuated, the control element is locked, and a previously effected bending of the bendable shaft is held in this position of bending. The operator does not have to concentrate on ensuring the locking position. It is only when a change is wanted that the actuating element has to be actuated and the locking action is in this way released and the control element moved to and fro within its pivot range, either for straightening the shaft or for bringing the bendable end to another position within its pivot range. After the actuating element is released, the lock is once again closed.

This increases the safety of handling of the medical instrument also in the sense that manipulations can be performed in a defined position of bending, for example a dissecting procedure or a coagulation procedure, without the degree of bending being changed.

In a further embodiment of the invention, the friction element is arranged on the handle.

This measure has the advantage that the friction element can be fastened on a relatively large structural part of the medical instrument, resulting in a correspondingly large and solid abutment with respect to the frictional forces.

In a further embodiment of the invention, the actuating element is arranged on the pivotable control element.

In ergonomic terms, this has the considerable advantage that one and the same element can be used both to control the bend control mechanism and also to release or effect the locking action. It is ergonomic particularly in view of the fact that a pivoting of the control element first requires release of the locking mechanism, since otherwise it cannot be moved, and it is therefore particularly expedient to combine the two structural elements necessary for this, namely the actuating element and the control element.

In a further embodiment of the invention, the friction element is pretensioned in the direction of the control element.

This measure has the advantage that the frictional force for the locking frictional engagement is made available by the pretensioning of the friction element, which is also very favourable from the point of view of production and control.

If the construction is such that there is a relatively high restoring force in the bend control mechanism, the pretensioning can then be chosen to be correspondingly great in order to ensure a secure locking action. It is thus possible to react in a flexible way to different operating inserts in the shaft and to different sizes and lengths of the shaft.

In a further embodiment of the invention, the friction element is designed as a friction plate which can be urged via spring plates in the direction of the control element.

This measure has the advantage that the friction plate can provide a relatively large and variable friction surface via which the pivotable control element can be moved within its pivot range. The provision of the pretensioning in the direction of the control element by means of spring plates is very simple from the production point of view, for example by using suitable punched parts, which can also be easily mounted or replaced.

In a further embodiment of the invention, the spring plates are designed as angled pieces arranged on the ends of the friction plate.

These measures particularly have the aforementioned advantage of simple production.

In a further embodiment of the invention, the friction plate has, at its ends, elongate openings via which it can be mounted on an outer face of the handle.

This measure has the advantage that the friction plate, particularly when it is curved, is able to execute the deflection or displacement movement via the elongate openings. It is also easy to fit the friction plate in place via this elongate opening, for example using simple assembly screws.

In a further embodiment of the invention, an underside of the control element is in contact with the friction element via a friction contact face.

This measure has the advantage that the friction contact face is relatively well protected from the outside and, in particular, does not occupy other sides of the control element, such that the necessary manipulations on the control element, i.e. the movement and control of the locking mechanism, can be performed without obstruction.

In a further embodiment of the invention, the control element has a finger-receiving part, and the actuating element is arranged in the finger-receiving part.

This embodiment is particularly ergonomic in the sense that a finger of the hand that is holding the medical instrument can be placed into this finger-receiving part, and this finger can be used both to operate the actuating element for releasing the locking mechanism and also to move the control element for bending the shaft. Depending on the arrangement of the control element on the medical instrument, this finger can, for example, be the thumb of said hand.

In a further embodiment of the invention, the actuating element is designed as a trigger via which the friction element can be moved out of the locking engagement away from the control element.

This measure has the advantage that, by a simple trigger action, the locking mechanism is released and the control element can then be pivoted.

The aforementioned pretensioning of the friction element in the direction of the control element means that, after release of the trigger, the latter is moved back again in the opposite direction, such that the locking mechanism closes again simply by release of the trigger. This can take place in any desired position in the pivot range of the control element, and of course also in the position in which the shaft is once again straight.

In a further embodiment of the invention, the trigger has at least one pin which bears on the friction element.

This measure has the advantage that the force for releasing the locking mechanism can be applied to the friction element via at least one pin.

In a further embodiment of the invention, the at least one pin moves the friction element out of the locking engagement away from the control element and slides over the friction element during a pivoting of the control element.

This measure has the advantage that the pin or pins can run with relatively low friction over the friction element during the pivoting of the control element and, with the trigger depressed, keep this friction element away from the control element.

In a further embodiment of the invention, the pins can be guided in sleeves in the control element.

This measure has the advantage that, in the case of locking mechanisms with high locking forces, the pins are guided safely through the sleeves, such that they can be made relatively thin, in order to keep the sliding frictional forces as low as possible.

In a further embodiment of the invention, the pins are designed with low friction at least in the area in which they are in contact with the friction element.

This measure has the advantage that, with the control element pressed in, the at least one pin can slide with low friction over the friction element.

For this purpose, all of the pins can be made of a low-friction plastic material or can be covered by such a material, or they can be fitted onto a metal main body.

In a further embodiment of the invention, the actuating element has features that increase its grip.

The features are particularly advantageously chosen from elevations, depressions, grooves, flutings, hollows, punches and the like.

These features provide the operator with particularly good haptic contact between the finger and the control element, such that the control maneuvers can be performed safely and in an ergonomic manner.

Particularly in the aforementioned construction with the pins that run over the friction element when the locking mechanism is released, this frictional force can be overcome particularly effectively using these features, without any danger of the finger slipping from the control element on account of high resistance forces.

In a further embodiment of the invention, the control element is connected via a connecting arm to a drum on which control wires are fastened which effect the bending movement of the bendable end of the shaft.

This measure known per se has the advantage that the control movement of the control element can be transmitted to the drum ergonomically and in a smooth movement via the connecting arm, which drum then in turn moves the control wires smoothly and without jolts.

In a further embodiment of the invention, one end of a control wire is pushed into a fastening screw and is fixed in the latter by a fixing screw.

This measure has the advantage that the position and length of a control wire can be optimized or corrected via the fastening screw, after which this position is fixed in the fastening screw by means of the fixing screw.

In a further embodiment of the invention, the fastening screw is secured in place by a securing screw.

This measure has the advantage that the fit of the fastening screw on the drum is additionally secured by the securing screw. Assembly is also made easier. This interaction of the screws also in principle permits a readjustment or a tightening of the pulling wires or of the tension of the pulling wires in inspection procedures. After a defined adjustment, it is also possible for the screws to be secured additionally by adhesive. This too contributes to the movements of the control element of the actuating element being transmitted ergonomically and smoothly.

In a further embodiment of the invention, the drum has a circumferential groove via which the control wires can be guided to the fastening sites.

This measure also contributes to secure guiding of the pulling wires in the area of the drum, such that the pivoting movements can be transmitted safely and without jolts.

In a further embodiment of the invention, the drum is designed as a drum section.

This measure has the advantage that not a complete drum with a 360 degree circumferential face is necessary but only a section thereof which is sufficient to control the reciprocating movement of the control wires attached to the drum.

In a further embodiment of the invention, the drum section has a side face corresponding approximately to a quarter of a circle.

These measures have the advantage that compared to a complete drum a much smaller component can be used for moving the control wires. It was recognized that a movement in a range of 90 degrees is proper to control the bendable end of the shaft.

In a further embodiment of the invention, a guide roller is arranged close to the drum section for guiding a control wire to the circumferential face of the drum section.

This measure has the advantage that the control wire coming from the shaft can be guided safely via the guide roller to the circumferential face of the drum section. This assures a safe control with a small and non-bulky construction.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which:

FIG. 1 shows a side view of a medical instrument with a bendable shaft,

FIG. 1a shows the medical instrument in FIG. 1 from the proximal direction, i.e. as seen by the operating surgeon, FIG. 4 shows a partial detail of the handle to illustrate the locking of a bend control mechanism, FIG. 4a shows the detail from FIG. 4, with a sectional view through a control element of the bend control mechanism in the locked state, FIG. 5 shows the detail as in FIG. 4a, in the state when not locked.

FIG. 13 shows a side view of a grip part of the instrument shown in FIG. 1, FIG. 13a shows a view of the grip part seen from the direction of the arrow 134 in FIG. 13, FIG. 14 shows an enlarged partial cross section along the line XIV-XIV in FIG. 13, with the end of the flexible insert from FIG. 11 in the locked state, FIG. 14a shows a view corresponding to FIG. 14, with the end of the flexible insert released, FIG. 15 shows an enlarged partial cross section along the line XV-XV in FIG. 13a, with the end of the flexible insert from FIG. 11 engaged, FIG. 16 shows a perspective view of a catch on its own.

DETAILED DESCRIPTION OF PREFERRED EMBODIMENTS

Figure 1B:
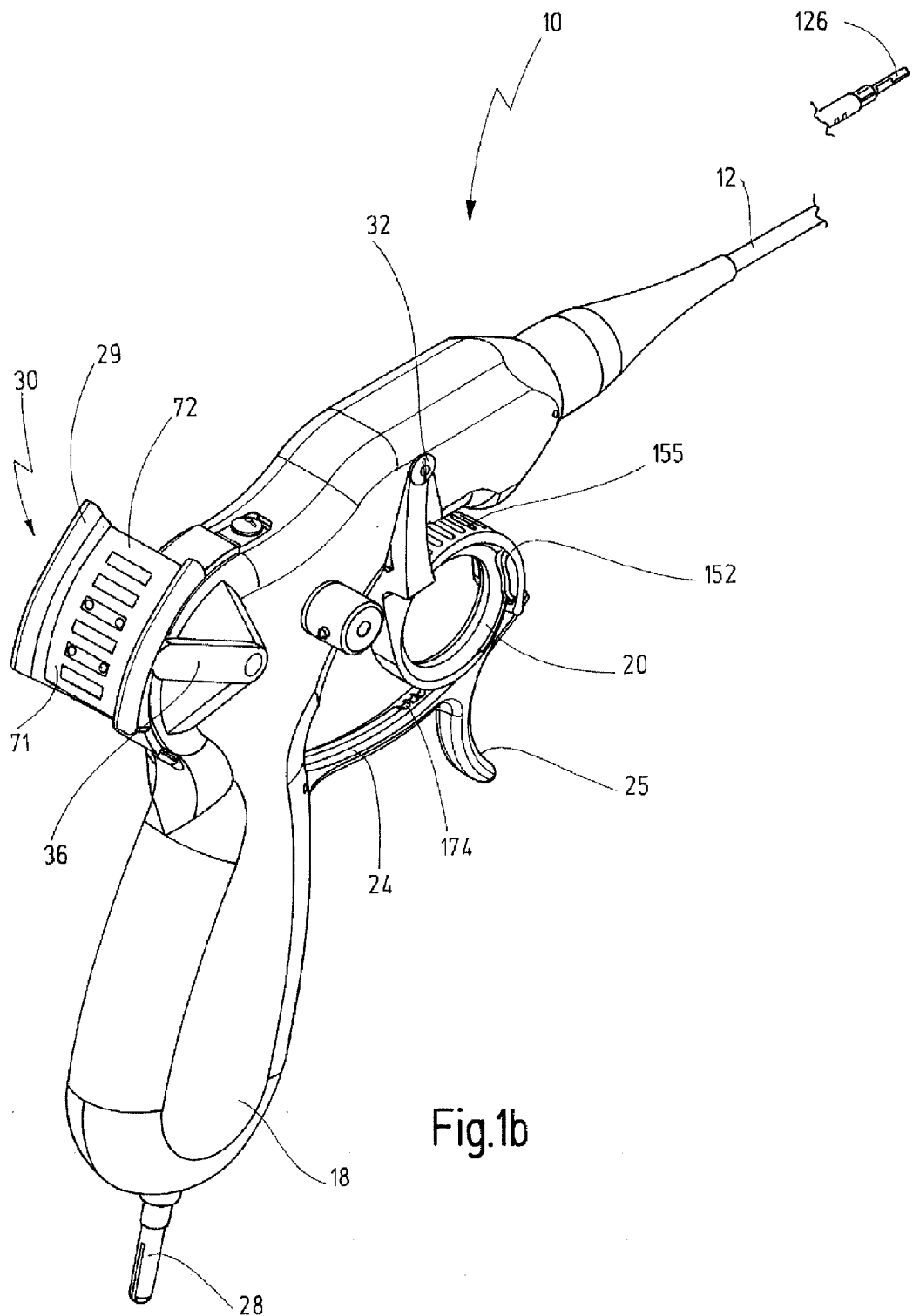
FIG. 1b shows a perspective view of the medical instrument.

A medical instrument as shown in the figures is designated in its entirety by reference sign 10.

The medical instrument 10 shown in FIG. 1 comprises a flexible shaft 12 which has a bendable area 14 at its distal end. A tool 126 is arranged distally on the area 14. The tool 126 constitutes a distal end of an insert 22 shown in FIG. 11. The proximal end of the shaft 12 is connected to a handle 18.

The handle 18 in turn comprises a movable grip part 20. The latter has a round opening 21 which is delimited by a ring portion 23 and through which preferably the index finger of the operating surgeon can be guided in order to execute a movement of the grip part 20, which is pivotable about the pivot axis 32 shown in FIG. 2. The grip part 20 is connected to the proximal end of the insert 22. By virtue of the connection of the grip part 20 to the insert 22, it is operatively connected to the tool 126 and thus serves to actuate the latter, e.g. to open and close a jaw part.

Moreover, the grip part 20 can be brought into contact with a lock 24 that can prevent unwanted movement of the grip part 20 in a distal direction. To permit a release of the lock connection, the lock 24 has, among other things, an arc-shaped attachment 25 which permits a pivoting movement of the lock 24 by the operating surgeon, preferably with the middle finger, as is described in connection with FIG. 17 et seq.

Moreover, the handle 18 is provided with a control element 29 of a bend control mechanism 30, the movement of which in the directions of the double arrow 31 about a pivot axis 38, running perpendicular to the illustrated axis of the shaft 12, permits control of the bending of the bendable end 14 of the shaft 12. An example of the direction of bending is indicated in FIG. 1 by the angled end 14'.

FIG. 1a is a view looking at the control element 29 of the bend control mechanism 30 and at an actuating element 71 in the form of a trigger 72 located thereon. The trigger 72 can be actuated by a thumb of the operating surgeon, as a result of which a movement of the control element 29 is permitted. To provide better grip, grooves 73 are arranged for this purpose on the trigger 72.

The instrument 10 also has a current attachment 28, which can be used, for example, to supply current to optional coagulation inserts.

Figure 2:
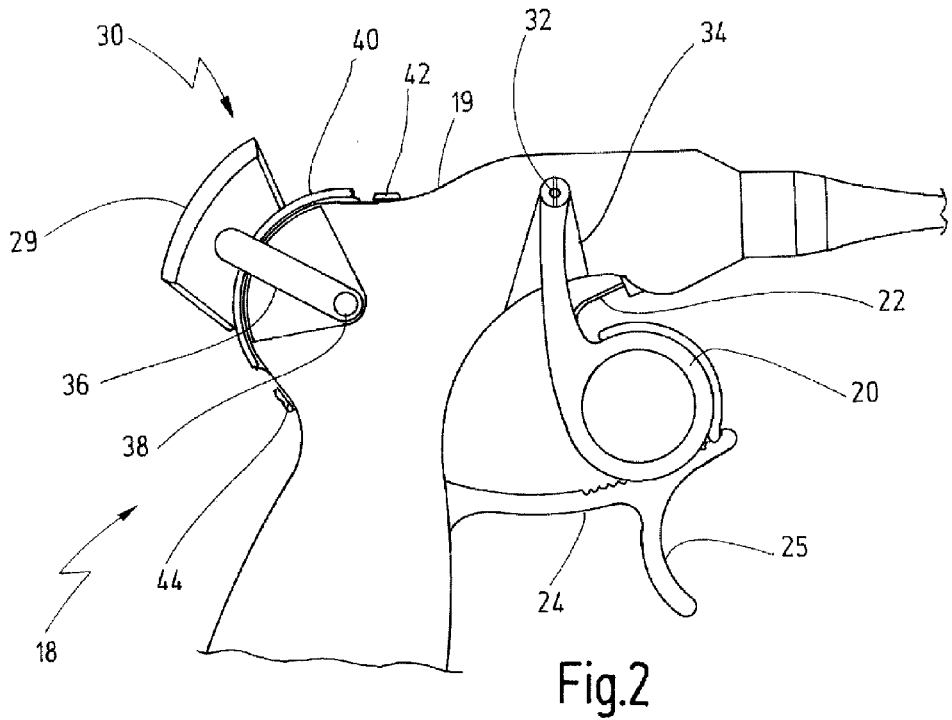
FIG. 2 shows a partial side view of the medical instrument in FIG. 1, from the opposite side.

FIG. 2 indicates the range of pivotability of the grip part 20 about the pivot axis 32 in the area of a recess 34. The control element 29 is connected to the pivot axis 38 via a connecting arm 36.

Between a housing 19 of the handle 18 and the control element 29, there is a friction element in the form of a friction plate 40, which is fastened to the outer face of the handle 18 by screws 42 and 44. As will be described in more detail below, this friction plate 40 is used to stop the bend control mechanism 30 in a defined position.

Figure 3:
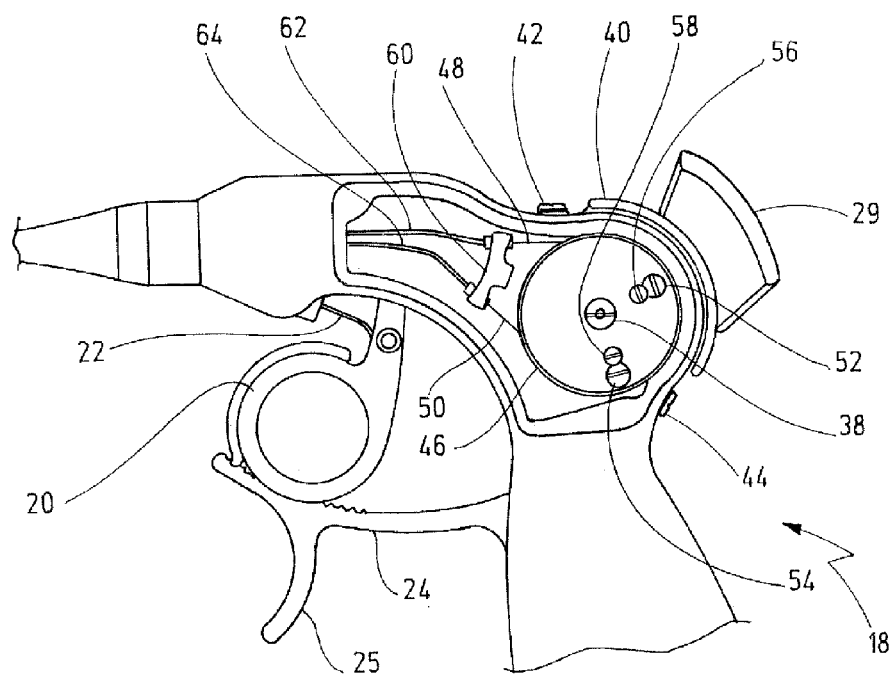
FIG. 3 shows a partial side view of the medical instrument in FIG. 1, with the housing of the handle opened.

A drum 46 shown in FIG. 3 is secured on the pivot axis 38 and is thus operatively connected to the control element 29 of the bend control mechanism 30 via the connecting arm 36. A corresponding actuation of the control element 29 thus also results in movement being transferred directly to the drum 46. Two control wires 48 and 50 extending through the shaft 12 from the bendable end 14 of the shaft 12 end on the drum 46, said wires 48 and 50 each extending to the sides of the pivot axis 38 and, in this illustrative embodiment, being fastened on the drum by fastening screws 52 and 54 in combination with securing screws 56 and 58. For this purpose, the control wires 48 and 50, emerging from sleeves 62 and 64, are conveyed through a guide 60 to the drum 46. The control wires 48 and 50 are the actuating elements for the bendable end 14. Together with the drum 46 and the connecting arm 36, they thus provide the operative connection between the control element 29 of the bend control mechanism 30 and the bendable end 14. A more detailed description of their function is given later in connection with FIG. 9.

The feature whereby the bend control mechanism 30, and thus the bendable end 14 of the shaft 12, can be locked with the aid of the friction plate 40 will now be described in detail in connection with FIGS. 4 to 8.

FIG. 4 shows that an underside 33 of the control element 29 is in direct contact with the friction plate 40, which is fastened on the handle 18 via angled spring plates 66 and 68 and by means of the screws 42 and 44. The friction plate 40 thus extends at a spacing from the outside of the handle 18 on which it is mounted. A movement of the control element 29 about the pivot axis 38 in the directions of the double arrow 70 is avoided or braked by the frictional contact between the control element 29 and the friction plate 40 on a friction contact face 82.

FIG. 4a shows that the bend control mechanism 30 comprises the trigger 72. The latter, as can also be seen in FIG. 1b, is easily accessible to the operating surgeon from the proximal direction. Protruding from the trigger 72 are pins 74, 74', 76, 76' (see also FIG. 7) which at the distal end are guided through and held by sleeves 78, 80 in the body of the control element 29. The tips of the pins bear directly on the friction plate 40 and thus provide an operative connection between the trigger 72 and the friction plate 40. By pressing the trigger 72 in the direction of the arrow 84, the pins are moved axially through bores 98, 100 in the body of the control element 29, and they thus press the friction plate 40 in the direction of the handle 18. The friction plate 40 thus moves away from the underside 33 of the control element 29. The friction contact face 82 is thus freed and a gap 86 is formed, as is shown in FIG. 5. The flexibility needed for this change of position of the friction plate 40 is permitted principally by the spring plates 66 and 68, but also by elongate openings 102 and 104, as are shown in FIG. 8.

The position resulting from the actuation of the trigger 72, as shown in FIG. 5, now permits a low-friction movement of the control element 29, as is shown by the double arrow 70 in FIG. 4.

Only the tips of the four pins 74, 74', 76, 76' rest on the friction plate 40 and slide with low friction across the surface thereof. For this purpose, they can be made of a low-friction plastic material, for example. It is also possible for a metal main body to be covered by the low-friction material, or for a low-friction tip to be fitted onto a metal stump.

When the operating surgeon now takes his finger, preferably the thumb, off the trigger 72, the tension afforded by the spring plates 66 and 68 means that the friction plate 40 is pressed back against the underside 33 of the control element 29 of the bend control mechanism 30, such that the gap 86 disappears and the friction contact face 82 is once again present. Correspondingly, the pins 74, 74', 76, 76' and thus the trigger 72 also undergo a proximal movement in the direction of the arrow 88. In this way, the bend control mechanism 30 is locked in its position again. This can therefore be done steplessly within the pivot range of the control element 29.

Figure 6:
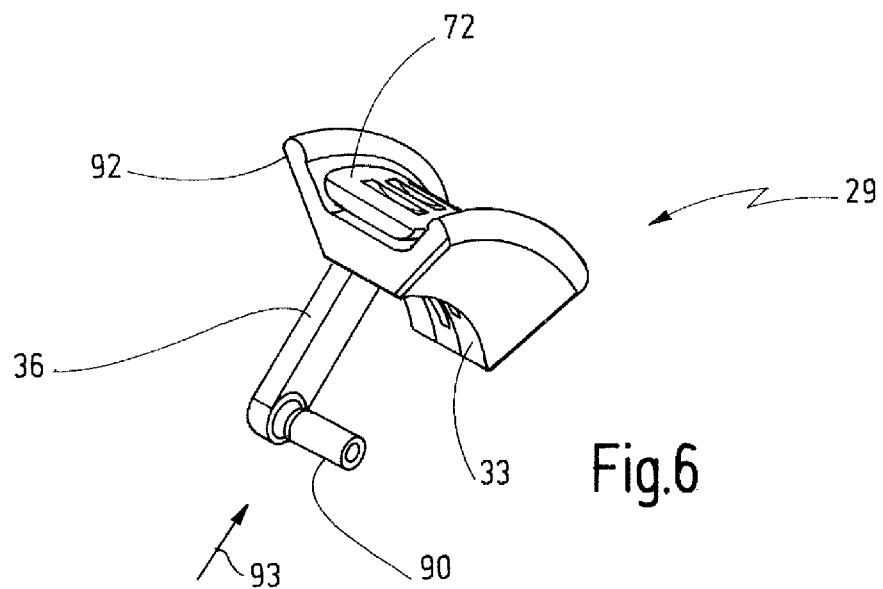
FIG. 6 shows the control element of the bend control mechanism in a perspective view on its own.
Figure 6A:
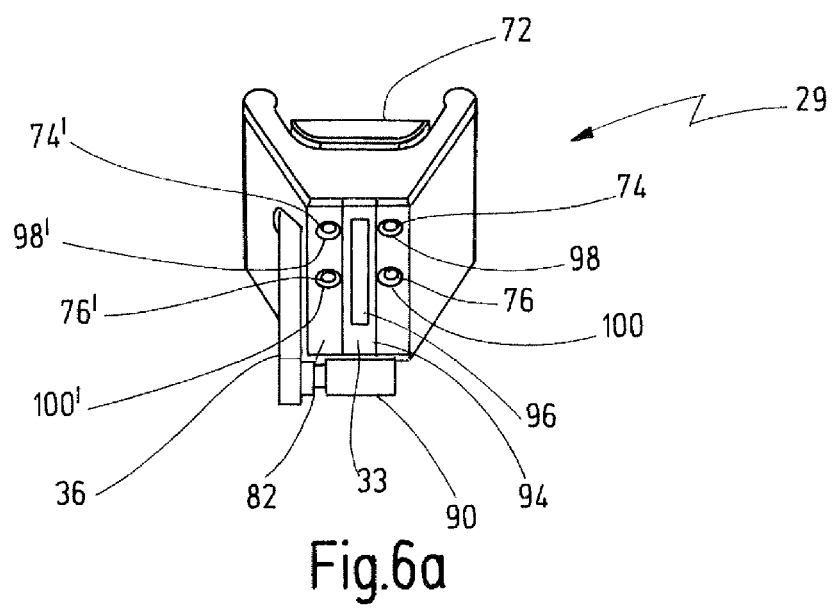
FIG. 6a shows a view of the control element from FIG. 6 along the arrow 93 in FIG. 6.
Figure 7:
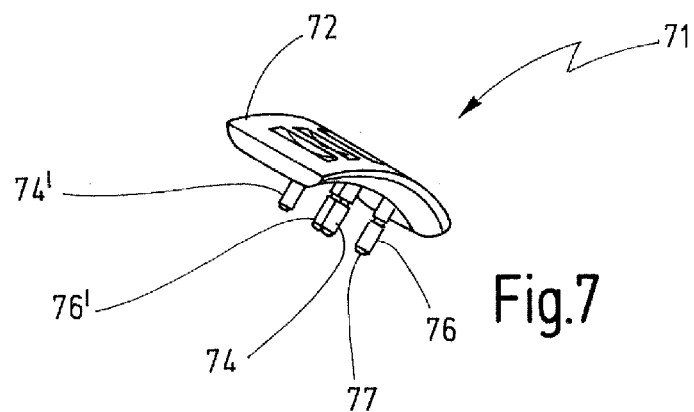
FIG. 7 shows an actuating element of the bend control mechanism in a perspective view on its own.
Figure 8:
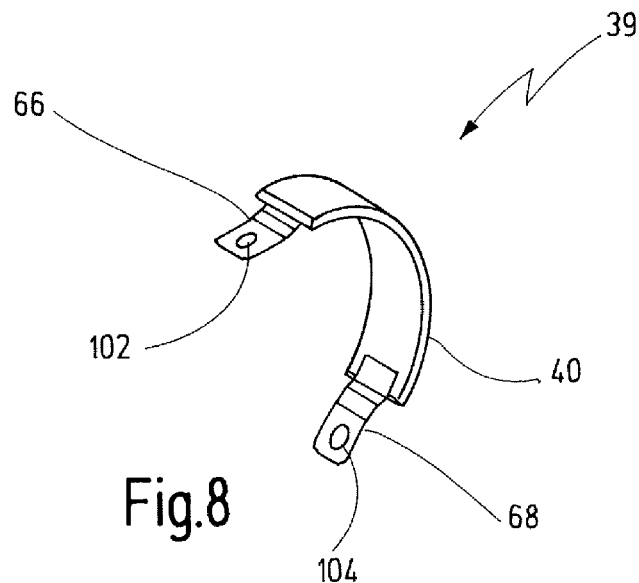
FIG. 8 shows a perspective view of a friction element for locking the bend control mechanism.

The control element 29 of the bend control mechanism 30 is shown in more detail in FIGS. 6, 6a and 7, in which the trigger 72 and the proximal access to the latter can be clearly seen. The trigger 72 is fastened on a finger-receiving part 92 which is mounted on the pivot axis 38 via the connecting arm 36 and with a pin 90.

FIG. 6a shows the underside 33 which comes into contact with the friction plate 40. In this illustrative embodiment, the trigger 72 is equipped with four pins 74, 74', 76 and 76', which extend axially and are movable within the bores 98, 98', 100 and 100'. Arranged between the two pairs of pins 74, 76 and 74', 76', there is a plastic inlet piece 96 which is fastened on the finger-receiving part 92 by a retaining plate 94. This plastic inlet piece 96 serves to increase the friction between the control element 29 and the friction plate 40 and, thereby, reinforce the locking in the desired position.

The trigger 72 with the four pins 74, 74', 76 and 76' can be seen clearly in FIG. 7. By virtue of their distally rounded tips 77, the friction as they slide on the friction plate 40 is reduced to a minimum, which facilitates the use of the bend control mechanism 30.

The illustrative embodiment of the friction element 39 with the friction plate 40 shown in FIG. 8 is connected at the opposite ends to the angled spring plates 66 and 68, which both have an elongate opening 102, 104, respectively, and this permits a mobility of the friction plate 40 on the handle 18, according to the above description, in other words towards and away from the handle 18. The angles on the spring plates 66 and 68 provide for the corresponding pressing force and, consequently, for the firm locking between the control element 29 and the handle 18 on which the friction plate 40 is mounted.

The function of the bend control mechanism 30 will be explained in more detail with reference to FIG. 9 to FIG. 10a, and the fastening of the control wires 48 and 50 on the drum 46 will be described.

Figure 9:
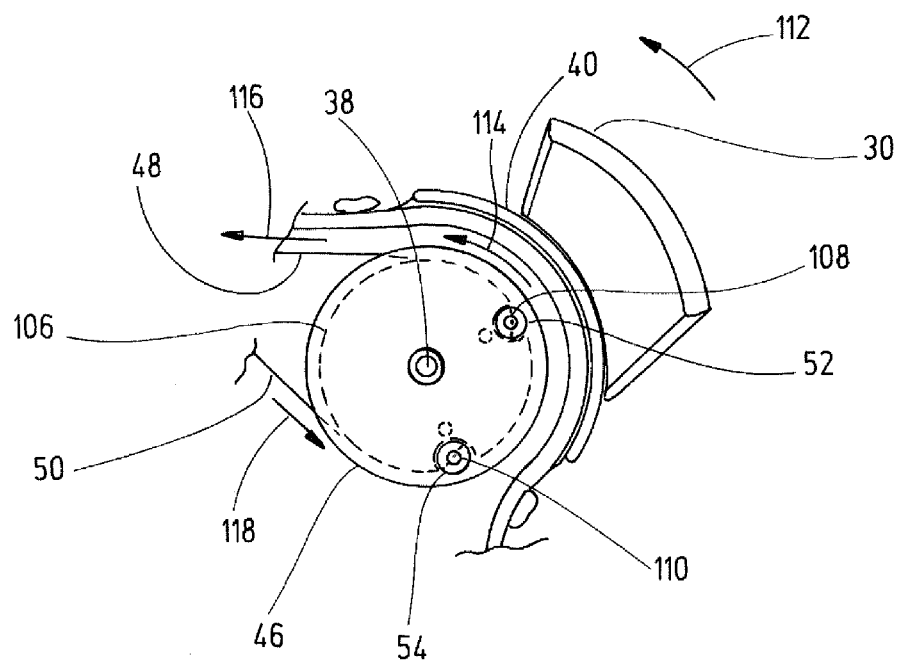
FIG. 9 shows a detail view as in FIG. 4, with control wires extending about a drum.
Figure 10:
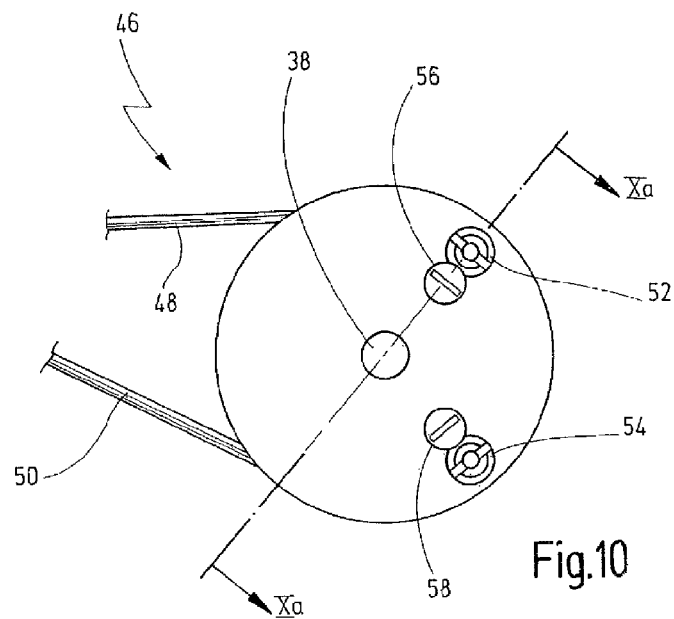
FIG. 10 shows a side view of the drum from FIG. 9.

FIG. 9 shows the course of the control wires 48 and 50 in the drum 46. The latter comprises a circumferential groove 106 in which the control wires 48 and 50 are guided, in order thereafter to end in bores 108 and 109 of the fastening screws 52 and 54. The control wires 48 and 50 are then mounted firmly on these.

If the control element 29 is now moved in the direction of the arrow 112, the drum 46, because of the above-described operative connection via the connecting arm 36, executes a rotation movement about the pivot axis 38, as is indicated by the direction of the arrow 114. For the control wires 48 and 50 secured on the drum 46, this means that they too execute a movement, specifically with the control wire 48 being pushed into the shaft 112 in the direction of the arrow 116 and with the control wire 50 being drawn out of the shaft in the direction of the arrow 118. As a result of the abovementioned operative connection of the control wires 48 and 50 to the bendable end 14, the angle setting of the latter is consequently changed. This results in a bending movement of the form represented by the bendable end 14' in FIG. 1.

The opposite movement again leads to a straightening of the shaft 12 or an upward bending movement as seen in FIG. 1. The setting or angle of the bendable end 14 can be locked in any desired position by releasing the trigger 72.

If the arrangement of the drum and of the control element were turned through 90°, this would result, not in the "up-down" bending plane shown in FIG. 1, but in a "left-right" bending plane turned 90° about the shaft axis. The control wires can also be arranged the other way round, in which case, for example, a "forward" displacement of the control element 29 leads to an "upward" bending movement instead of a "downward" bending movement.

Figure 10A:
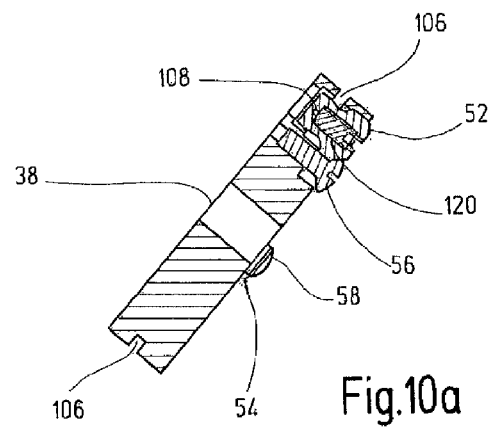
FIG. 10a shows a cross section along the line Xa-Xa in FIG. 10.

FIG. 10a shows the circumferential groove 106. It also shows the bore 108 of the fastening screw 52. Through this, in the example mentioned here, the control wire 48 is inserted into the fastening screw 52 and mounted firmly in this fastening screw by means of a fixing screw 120. The same applies to the fastening screw 54, not shown here in the cross section, and to the control wire 50. The length of the control wires 48 and 50 can then be adjusted by individual rotation of the screws 52 and 54. In one illustrative embodiment, these have mutually different threads for this purpose, such that fastening screw 52 has a right-hand thread and fastening screw 54 has a left-hand thread. After the control wires 48 and 50 have been adjusted, the fastening screws 52 and 54 are fixed by means of the securing screws 56 and 58. These prevent independent rotation of the fastening screws 52 and 54 and thus prevent unwanted adjustment of the control wires 48 and 50.

Figure 10B:
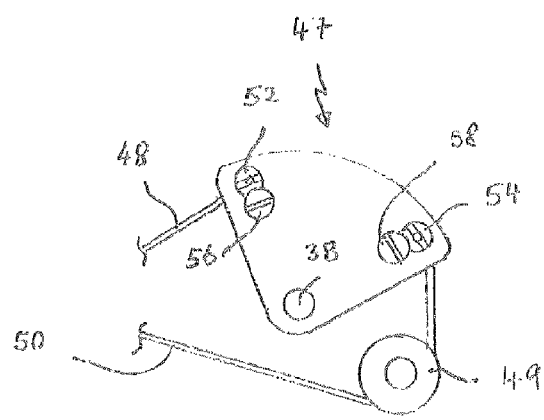
FIG. 10b shows a further embodiment of a drum as a drum section.

FIG. 10b shows a further embodiment of a drum. The drum 47 differs from drum 46 in that the drum 47 is only a section which corresponds approximately to a quarter of the drum 46. The lateral side face of drum 47 corresponds to a circle section having an angle of about 90 degrees.

The pivot axis 38 and the mounting of the control wires 48 and 50 via the fastening screws 42 and 54 and the securing screws 56 and 58 is identical. For guiding the control wire 50, a guide roller 49 is provided.

This embodiment is rather bulky, therefore the medical instrument 10 is less bulky in the area of the drum. A pivoting movement of the drum 47 as a drum section is sufficient for controlling the movement of the bendable end 14 of the shaft.

In FIGS. 11 to 16, the design and assembly of the flexible insert 22 are described.

Figure 11:
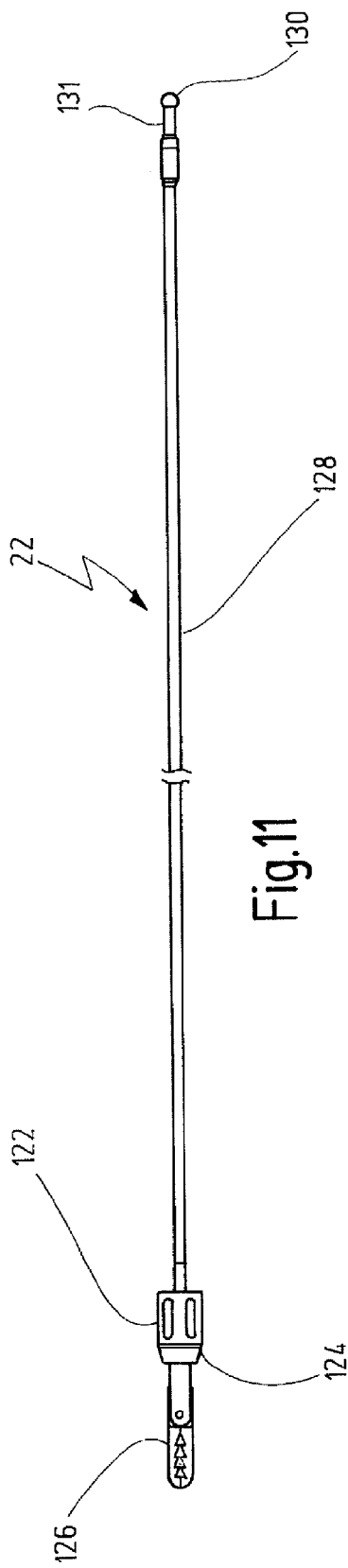
FIG. 11 shows a side view of a flexible insert for the medical instrument in FIG. 1.

The insert 22 shown in FIG. 11 has at its distal end a tool 126, in this case two spreadable jaw parts 127, 127', which tool is operatively connected to a connection piece 130 via a rod-shaped flexible actuating element 128. Mounted proximally behind the tool 126, there are a hood 124 and a screw closure 122 which both serve to fasten the insert 22 on a flexible shaft, e.g. on the flexible shaft 12 from FIG. 1 in an axially immovable manner. As has already been mentioned, the proximal end of the insert 22 has the connection piece 130, which serves, for example, for fastening on the grip part 20 of the medical instrument 10. For this purpose, in this illustrative embodiment, the end has a spherical shape and is arranged proximally behind a portion 131 of smaller diameter on the insert 22.

Figure 12:
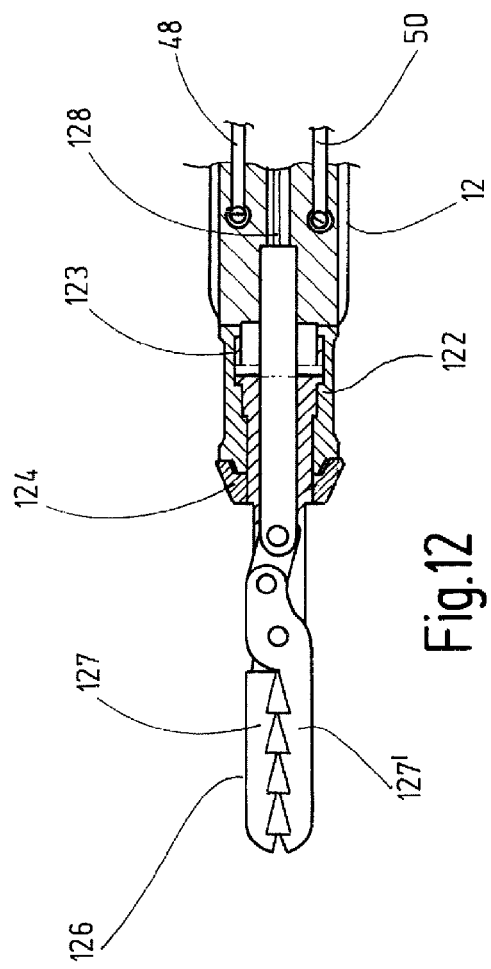
FIG. 12 shows an enlarged detail view of the distal end of the tool of the flexible insert.

FIG. 12 shows the fastening of the distal end of the insert 22 on the distal end of the shaft 12. The hood 124 located proximally behind the tool 126 is connected firmly to the insert 22. This prevents the screw closure 122 from slipping in a distal direction. This screw closure 122 is for its part then screwed onto an outer thread 123 at the distal end of the shaft 12. For this purpose, the force transmission element 128 is first inserted from the distal direction into the shaft 12. The distal end of the insert 22 is fixed in position by this fastening. A bending of the bendable end 14 then no longer causes the insert 22 to be pushed out from the distal end of the shaft 12.

FIGS. 13 to 16 show the grip part 20, the pivot axis 32 thereof and a catch 132 for releasable connection to the proximal end of the insert 22. FIG. 13a shows an opening 136 which opens in the direction of the pivot axis 32 and through which the spherical end of the connection piece 130 is inserted. The portion 131 of small diameter following distally from this on the insert 22 can be guided out laterally from the interior of the grip part 20 via a groove 138 (see FIG. 15). To introduce the end of the insert 22, a catch 132 has to be pressed such that the connection piece 130 can pass the latter. This can be seen from FIGS. 14 and 14a.

The catch 132 shown in FIG. 16 is held by a retainer 146 on the grip part 20. It is further pressed against the edge of this retainer 146 by a spring 148. The position shown in FIG. 14 thus represents the starting position of the catch 132. It will be seen how the connection piece 130, because of its spherical end here, is blocked by the catch 132 and therefore cannot pass upwards, with reference to the drawing, through the opening 136. If the catch 132 is now actuated counter to the direction in which it is pressed by the spring 148, that is to say in the direction of the arrow 147, a recess 144 which is provided on the catch 132, which is located to the right of the connection piece 130 in the view in FIG. 14, moves into a central position of the opening 136, as is shown by way of example in FIG. 14a. This pressing-in can be done via a knob 145 which protrudes laterally outwards past the retainer 146. This recess 144 gives the spherical connection piece 130 enough room to move past this catch 132. In this way, the connection piece 130 can be removed from the retainer in the grip part 20 by way of the opening 136. When the catch 132 is released again, it moves back out again in the direction of the arrow 149 in FIG. 14a. The reason for this is once again the spring 148. At the same time, the recess 144 also moves then.

If the connection piece 130 is then to be fitted back into the retainer of the grip part 20, the catch 132 has to be pressed back in the direction of the arrow 147 in FIG. 14, such that the recess 144 comes to lie once more in the central position, as is shown in FIG. 14a. In this way, the spherical end can be guided past the catch 132 again, and the connection piece 130 can be fastened on the grip part 20 via the opening 136.

FIG. 15 shows how a connection piece 130 is located under the catch 132. An upward movement is not possible. The portion 131 of small diameter on the proximal end of the insert 22 fits through the groove 138, thus permitting mobility in the direction of the double arrow 151. This freedom of movement is needed in the movement of the grip part 20.

To avoid a rotation of the catch 132 pivotable about the longitudinal axis, and thus also to avoid a rotation of the recess 144, an axial groove 142 is formed at the distal end of the catch 132. This groove 142 also serves as an abutment for the displacement movement. This is shown in FIGS. 14 and 14a, and also in the perspective view in FIG. 16. A pin 140 now ends in this groove 142 upon fastening in the grip part 20 and, although it prevents undesired rotation about the longitudinal axis of the catch 132, it nevertheless permits an axial mobility of the catch 132 in the direction of the arrows 147 and 149.

In FIGS. 17 to 20, the lock connection formed by the lock 24 on the grip part 20 is shown in detail.

The lock 24 is mounted in a recess 163 on the handle 18 so as to be pivotable about a pivot axis 150. In this illustrative embodiment, this lock 24, by contact with the grip part 20, can suppress the movement of the grip part 20 in the distal direction. For this purpose, the lock 24 is pressed in the direction of the grip part 20 by the pretensioning afforded by a spring plate 166.

For this purpose, the lock 24, on its side directed towards the grip part 20, has locking teeth 174 which come into engagement with a locking pin 160 on the grip part 20. The inclination of the flanks of the locking teeth 174 in the direction of the handle 18 permits a movement of the grip part 20 in the direction of the handle 18, but blocks this in the opposite direction.

Figure 18:
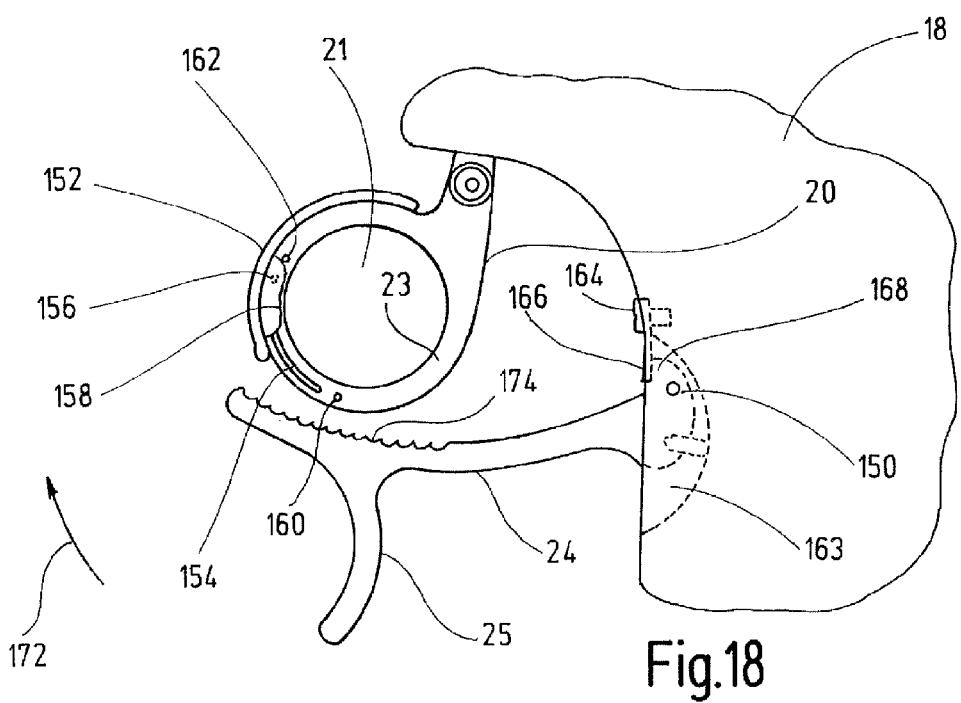
FIG. 18 shows a view corresponding to FIG. 17, with the lock connection released.

If the lock connection is to be released briefly, the lock 24 is pivoted in the direction of the arrow 170, preferably by actuation via the arc-shaped attachment 25, which leads to an end position as shown in FIG. 18. Because of the pretensioning, the lock 24, when released, is brought back again to the grip part 20 in the direction of the arrow 172.

In order to deactivate the lock connection for a period of time, a detent 152 is provided on the grip part 20.

The detent 152 is designed as a curved element, in the illustrative embodiment shown here as a curved strip 153 (see also FIG. 13a) whose curvature is adapted to the curvature of the outer face of the ring section 23 of the grip part 20.

Recesses or punches 155 in the strip 153 increase its grip.

Figure 17:
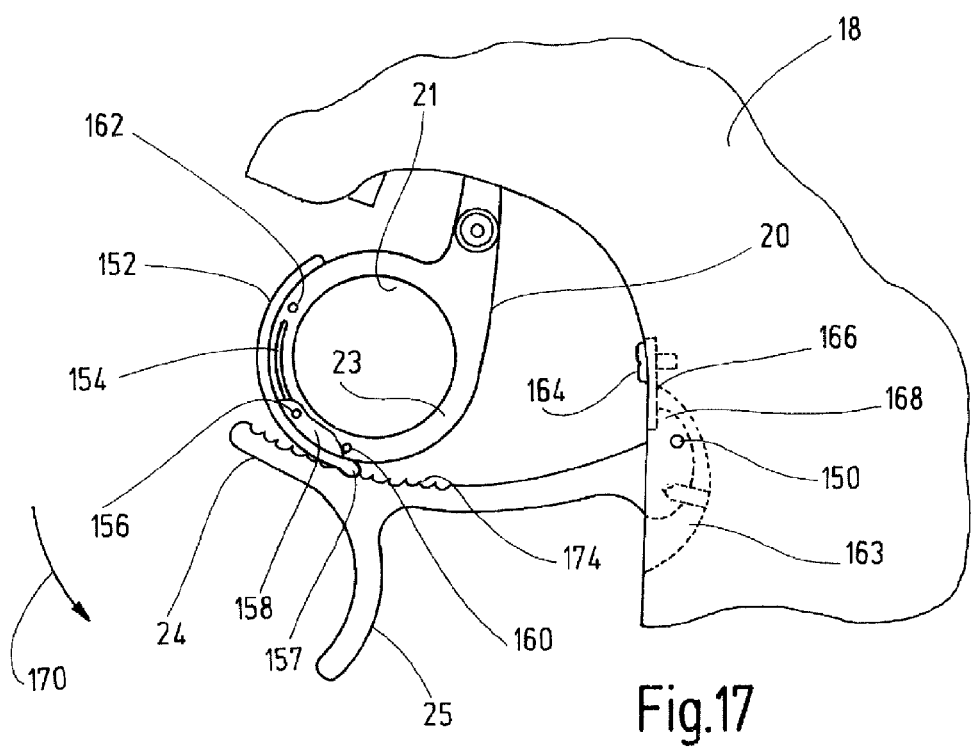
FIG. 17 shows a detail view of a medical instrument in the area of the grip part in order to illustrate the lock connection.

As can be seen in FIG. 17, this detent 152 can be brought between grip part 20 and lock 24. In this case, the lock connection is deactivated and the grip part 20 is movable freely in both directions. For this purpose, the detent 152 has a rounded nose 157, which can run in both directions over the teeth 174. This corresponds to a second position of the detent 152. In order now to reactivate the lock connection, the detent 152 can be pushed in the direction of a locking pin 162. This corresponds to a first position of the detent 152. A cover 158 is provided on both sides of the strip 153. This cover 158 conceals a guide pin 156 which extends transversely in the detent and which runs in guide grooves 154 on both sides of the ring section 23. The covers 158 themselves can be fastened on the detent 152 by pins (not shown here). Accordingly, the detent 152 extends through a circular movement, as is defined by the shape of the ring section 23 of the grip part 20, and thus ends in a position as shown in FIG. 18. In this way, a locking pin 160 previously blocked by the detent 152 now lies free and can come into engagement with the teeth 174 of the lock 24.

Figure 19:
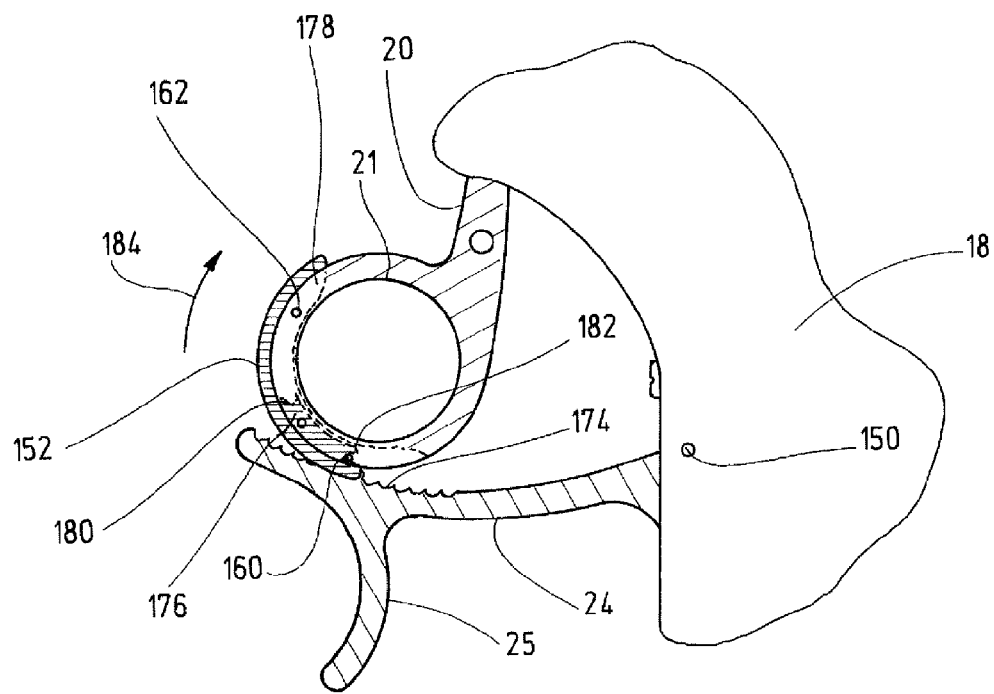
FIG. 19 shows a view corresponding to FIG. 17, as a cross section seen in the viewing plane and with the lock connection deactivated.
Figure 20:
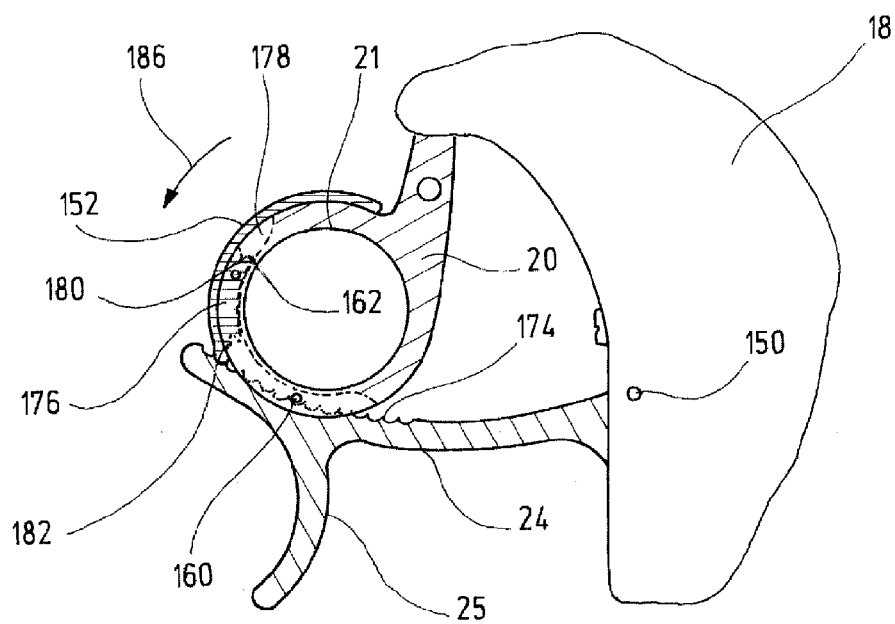
FIG. 20 shows a view corresponding to FIG. 19, with the lock connection activated.

As is shown in FIGS. 19 and 20, an outer groove 178 is cut into the circumference of the grip part 20. A step 176 of the detent 152 projecting in the radial direction of the ring section 23 can be moved in this groove 178, which step 176 is arranged centrally on the detent 152. Spring clips 180 and 182 are arranged respectively at each end of this step 176. They are able to engage in the locking pins 160 and 162, respectively, in accordance with the position of the detent 152 and thus prevent a simple reciprocating sliding of the detent 152. The latter is thus held in the respective positions.

FIG. 19 shows, in this connection, the second position of the detent 152, in which the lock connection is deactivated. The spring clip 182 of the step 176 on the detent 152 is engaged in the locking pin 160 and thus blocks the contact between the locking teeth 174 and the locking pin 160. A movement of the detent 152 in the direction of the arrow 184 would finally end in the first position, as is shown in FIG. 20. The spring clip 180 located on the step 176 is engaged in the locking pin 162, and the detent 152 is thus fixed in this position. The locking pin 160 thus lies free and is able to hook into the teeth 174 of the lock 24.

By contrast, a proximal movement of the grip part 20, which would lead for example to a closing of the jaw parts 127, 127', is again possible via the lock 24.

The lock connection can now be deactivated again by moving the detent 152 analogously to what has been stated above in the direction of the arrow 186, preferably after the lock 24 has been lowered, in accordance with the description of FIGS. 17 and 18.

As can be seen in FIG. 1a, the operator can hold the instrument 10 via the handle 18. The trigger 72 can be pressed by the thumb and the control element 29 then displaced. This causes a corresponding bending of the bendable end 14 of the shaft. Release of the trigger 72 stops the bendable end 14 in the corresponding position.

A movement of the grip part 20, e.g. by the inserted index finger, permits the opening and closing of the jaw parts 127, 127' via the insert 22 in any desired angled position of the bendable end 14 of the shaft 12.

When the lock function is deactivated, the movement of the grip part 20 is possible in both directions of pivoting.

When the lock function is activated, this can be quickly obtained by pivoting the lock 24 with the middle finger via the arc-shaped attachment 25.

The operator is thus able to manoeuvre the medical instrument 10 easily and safely and in a highly ergonomic manner.

What is claimed is:

1. A medical instrument comprising
a shaft having a distal end being bendable,
a handle arranged at a proximal end of said shaft,
a bend control mechanism for controlling a bending movement of said bendable distal end of said shaft, said bend control mechanism being arranged at said handle and having a pivotable control element, a pivoting of said pivotable control element causes a bending of said bendable distal end of said shaft, and
a locking mechanism for locking said bend control mechanism in defined positions, wherein
said pivotable control element runs over a friction element, wherein
an actuating element being provided via which said friction element can be brought out of the locking engagement with said pivotable control element,
wherein
said friction element is designed as a friction plate pretensioned in a direction of said control element, wherein said control element has a finger-receiving part wherein said actuating element is arranged within said finger-receiving part,
wherein said friction plate can be urged via spring plates in a direction of said control element, and wherein said spring plates are designed as angled pieces arranged on ends of said friction plate.

2. The medical instrument of claim 1, wherein said friction element is arranged on said handle.

3. The medical instrument of claim 1, wherein said actuating element is arranged on said pivotable control element.

4. A medical instrument comprising
a shaft having a distal end being bendable,
a handle arranged at a proximal end of said shaft,
a bend control mechanism for controlling a bending movement of said bendable distal end of said shaft, said bend control mechanism being arranged at said handle and having a pivotable control element, a pivoting of said pivotable control element causes a bending of said bendable distal end of said shaft, and
a locking mechanism for locking said bend control mechanism in defined positions, wherein
said pivotable control element runs over a friction element, wherein
an actuating element being provided via which said friction element can be brought out of the locking engagement with said pivotable control element,
wherein
said friction element is designed as a friction plate pretensioned in a direction of said control element, wherein said control element has a finger-receiving part, wherein said actuating element is arranged within said finger-receiving part,
wherein said friction plate can be urged via spring plates in a direction of said control element, and wherein said friction plate has, at its ends, elongate openings via which said friction plate is mounted on an outer face of said handle.

5. The medical instrument of claim 1, wherein an underside of said control element is in contact with said friction element via a friction contact face.

6. The medical instrument of claim 1, wherein said actuating element is designed as a trigger via which said friction element can be moved out of said locking engagement away from said control element.

7. The medical instrument of claim 6, wherein said trigger has at least one pin bearing on said friction element.

8. The medical instrument of claim 7, wherein said at least one pin moves said friction element out of said locking engagement away from said control element and slides over said friction element during a pivoting of said control element.

9. The medical instrument of claim 7, wherein each pin can be guided in a sleeve in said control element.

10. The medical instrument of claim 7, wherein said at least one pin is designed with a low friction at least in an area in which said pin is in contact with said friction element.

11. The medical instrument of claim 1, wherein said actuating element has features that increase its grip.

12. The medical instrument of claim 11, wherein said features are chosen from the group of elevations, depressions, grooves, flutings, hollows, and punches.

13. The medical instrument of claim 1, wherein said control element is connected via a connecting arm to a drum on which control wires are fastened which effect a bending movement of said bendable end of said shaft.

14. The medical instrument of claim 13, wherein one end of a control wire is pushed into a fastening screw and is fixed in the latter by a fixing screw.

15. The medical instrument of claim 14, wherein said fastening screw is secured in place by a securing screw.

16. The medical instrument of claim 13, wherein said drum has a circumferential groove via which said control wires can be guided to fastening sites.

17. The medical instrument of claim 13, wherein said drum is designed as a section of a drum.

18. The medical instrument of claim 17, wherein said section of said drum has a side face corresponding approximately to a quarter of a circle.

19. The medical instrument of claim 17, wherein at least one guide roller is arranged beneath the drum designed as a section of a drum for guiding a control wire to a circumferential face of the drum section.

20. A medical instrument comprising
a shaft having a distal end being bendable,
a handle arranged at a proximal end of said shaft,
a bend control mechanism for controlling a bending movement of said bendable distal end of said shaft, said bend control mechanism being arranged at said handle and having a pivotable control element, a pivoting of said pivotable control element causes a bending of said bendable distal end of said shaft, and
a locking mechanism for locking said bend control mechanism in defined positions, wherein
said pivotable control element runs over a friction element, wherein
an actuating element being provided via which said friction element can be brought out of the locking engagement with said pivotable control element,
wherein
said friction element is designed as a friction plate which can be urged via spring plates in a direction of said control element, and wherein said spring plates are designed as angled pieces arranged on ends of said friction plate.

21. A medical instrument comprising
a shaft having a distal end being bendable,
a handle arranged at a proximal end of said shaft,
a bend control mechanism for controlling a bending movement of said bendable distal end of said shaft, said bend control mechanism being arranged at said handle and having a pivotable control element, a pivoting of said pivotable control element causes a bending of said bendable distal end of said shaft, and
a locking mechanism for locking said bend control mechanism in defined positions, wherein
said pivotable control element runs over a friction element, wherein
an actuating element being provided via which said friction element can be brought out of the locking engagement with said pivotable control element,
wherein
said friction element is designed as a friction plate which can be urged via spring plates in a direction of said control element, and wherein said friction plate has, at its ends, elongate openings via which said friction plate is mounted on an outer face of said handle.

* * * * *